(12) United States Patent
Zellerhoff (10) Patent No.: US 9,164,046 B2
(45) Date of Patent: Oct. 20, 2015

(54) METHOD FOR A THREE-DIMENSIONAL REPRESENTATION OF A MOVING STRUCTURE

(75) Inventor: Michael Zellerhoff, Forchheim (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 2144 days.

(21) Appl. No.: 12/221,942

(22) Filed: Aug. 7, 2008

(65) Prior Publication Data

US 2009/0041179 A1    Feb. 12, 2009

(30) Foreign Application Priority Data

Aug. 10, 2007  (DE) .......................... 10 2007 037 874

(51) Int. Cl.
*A61B 6/00* (2006.01)
*G01N 23/04* (2006.01)

(52) U.S. Cl.
CPC ............ *G01N 23/046* (2013.01); *A61B 6/4441* (2013.01); *A61B 6/466* (2013.01); *A61B 6/481* (2013.01); *A61B 6/504* (2013.01); *A61B 6/507* (2013.01); *A61B 6/541* (2013.01); *G01N 2223/419* (2013.01)

(58) Field of Classification Search
CPC .... A61B 8/06; G01S 15/8915; G01S 15/8984
USPC .......... 600/407, 425, 428, 431, 436; 378/4, 8, 378/19, 21, 22, 9, 100, 26, 11; 382/107–132
See application file for complete search history.

(56) References Cited

U.S. PATENT DOCUMENTS

2006/0120507 A1   6/2006 Brunner et al.
2006/0285632 A1   12/2006 Boese
(Continued)

FOREIGN PATENT DOCUMENTS

DE    10 2004 057 308 A1    7/2006
DE    10 2006 012 181 A1    9/2007
(Continued)

OTHER PUBLICATIONS

L.A. Foldkamp, L.C. Davis and J.W. Kress; "Practical cone-beam algorithm"; J. Opt. Sec. Am A; vol. 1, No. 6; Jun. 1984; pp. 612-619.
(Continued)

*Primary Examiner* — Mark Remaly (57) ABSTRACT

The invention relates to a method for three-dimensional representation of a moving structure by a tomographical method. Projection images are recorded by an image recording unit during a rotational run from recording angles between a start angle and an end angle, with a three-dimensional image data reconstructed from the projection images, with a first perfusion measurement with a first contrast agent injection and a first rotational run and with a further perfusion measurement with a further contrast agent injection and a further rotational run, which is started after the preceding perfusion measurement has concluded, with the start time and/or the start angle of the additional rotational run deviating from one another in respect of the time of the contrast agent injection. The method enables a functional three-dimensional time-resolved imaging of perfusion processes with the aid of flexible C-arm x-ray devices, which allow a functional imaging in an interventional environment.

17 Claims, 5 Drawing Sheets

(56) References Cited

U.S. PATENT DOCUMENTS

| | | |
|---|---|---|
| 2007/0232901 A1 | 10/2007 | Benndorf et al. |
| 2007/0253527 A1* | 11/2007 | Wink .............................. 378/11 |
| 2008/0025590 A1 | 1/2008 | Zellerhoff |

FOREIGN PATENT DOCUMENTS

| | | |
|---|---|---|
| DE | 10 2006 035 067 A1 | 1/2008 |
| JP | 10033516 A | 2/1998 |
| JP | 2003116839 A | 4/2003 |
| JP | 2006122549 A | 5/2006 |
| JP | 2006150080 A | 6/2006 |
| JP | 2006223427 A | 8/2006 |
| JP | 2007502645 A | 2/2007 |

OTHER PUBLICATIONS

Klaus Mueller, Roni Yagel, and John J. Wheller; "A Fast and Accurate Projection Algorithm for 3D Cone-Beam Reconstruction with the Algebraic Reconstruction Technique (ART)"; Presented at the SPIE Medial Imaging Conference, San Diego, CA; Feb. 21-27, 1998; pp. 1-9.

* cited by examiner

METHOD FOR A THREE-DIMENSIONAL REPRESENTATION OF A MOVING STRUCTURE

CROSS REFERENCE TO RELATED APPLICATIONS

This application claims priority of German application No. 10 2007 037 874.4 filed Aug. 10, 2007, which is incorporated by reference herein in its entirety.

FIELD OF THE INVENTION

The invention relates to a method for the three-dimensional representation of a moving structure by a tomography method.

BACKGROUND OF THE INVENTION

The three-dimensional imaging with C-arm x-ray devices was hitherto only implemented statically, i.e. without temporal information.

To this end, the C-arm rotates by approximately 200° (180°+fan angle) about the patient and in this way records between 50 and 1000 images of the patient. A three-dimensional image can be obtained from these recordings from different projection directions with the aid of a suitable reconstruction method, like for instance the filtered back projection, which is described in "Practical Cone-beam Algorithm" by Feldkamp et al., J. Opt. Soc. Amer. A, Vol. 1, No. 6, June 1984, pages 612 to 619, or the algorithm described by Klaus Mueller et al. in "A Fast and Accurate Projection Algorithm for 3D Cone-Beam Reconstruction with the Algebraic Reconstruction Technique (ART)".

Two rotational runs are generally implemented in order to represent vascular trees. A contrast agent is injected into the vessel to be displayed in the second rotational run. A three-dimensional image in which only the contrast agent-filled vessels are displayed is obtained by subtracting both runs and a subsequent reconstruction.

The functional imaging, like for instance perfusion imaging, is generally implemented using CT and MR. These imaging modalities are however generally not available in an interventional setting.

DE 10 2004 057 308 A1 relates to an angiographic x-ray diagnostics device for rotation angiography comprising an x-ray emitter which can be moved on a circular path, an opposing image detector unit which can be moved on a circular path, a digital imaging system for recording a plurality of projection images, a device for reconstructing a 3D volume image and a device for correcting physical effects and/or inadequacies in the recording system such as truncation correction, scattered radiation correction, irradiation correction, ring artifact correction, correction of the beam hardening and/or of the low frequency drop for the soft tissue representation of projection images and the 3D volume images reconstructed therefrom.

In the former patent application DE 10 2006 035 067.7, a method for the temporal and three-dimensional representation of a periodically changeable structure is described, in which several rotational exposures are created. The necessary rotational runs are started at an identical event of the period process offset by a specific angle. New image series are combined from the rotational exposures, whereby three-dimensional representations are reconstructed to form different phase regions of the periods.

SUMMARY OF THE INVENTION

The invention is based on the object of embodying a method such that a functional three-dimensional time-resolved imaging of perfusion processes with the aid of flexible C-arm x-ray devices is enabled, which allows a functional imaging in an interventional setting.

The method relates to a three-dimensional representation of a moving structure by a tomography method, with which a series of projection images are recorded by an image recording unit during a rotational run from different recording angles between a start angle and an end angle, with it being possible to reconstruct three-dimensional image data from the projection images.

The object is inventively achieved in accordance with the claims:
  comprising a first perfusion measurement with a first contrast agent injection and at least one first rotational run and
  at least one further perfusion measurement with a further contrast agent injection and at least one further rotational run, which is started after the preceding perfusion measurement has concluded,
  with the start time and/or the start angle ($\phi_0$) of the at least one further rotational run deviating from one another in respect of the time of the contrast agent injection.

It has proven advantageous in the case of an identical rotational direction of the image recording unit during N perfusion measurements for the individual delay times between the contrast agent injection and recording sequence of the nth perfusion measurement to be shifted by the n/Nth duration of a complete rotational exposure (rotation duration including return motion), compared with the first perfusion measurement.

In accordance with the invention, the delay time between the contrast agent injection and the recording sequence of the second perfusion measurement may be greater, but also smaller than the delay time with the first perfusion measurement.

The second perfusion measurement can advantageously be started temporally prior to the second contrast agent injection, i.e. the delay $\Delta T$ can be negative. As a result, a rotational exposure without a contrast agent can be created as a mask image.

Alternatively, in the case of opposite rotational directions of the image recording unit during the perfusion measurements, in accordance with the invention the perfusion measurements can however begin at the same start time, in respect of the injection time, however with a reverse start angle.

It has proven advantageous for the following steps to be implemented:
a) Start a first contrast agent injection,
b) Await a delay time (delay) $\Delta T1$,
c) Record several rotational exposures during rotational runs with the same rotational direction and return motion between the rotational runs,
d) Optional pause of any length
e) Start a second contrast agent injection
f) Await a delay time (delay) $\Delta T2 = \Delta T1 + \frac{1}{2}*(\text{rotation time} + \text{return motion time})$,
g) Record several rotational exposures during rotational runs with the same rotational direction and return motion between the rotational runs,
h) Interpolation of rotational exposures at fixed times $t_i$ from two perfusion measurements,
i) Reconstruction of three-dimensional data records at the times $t_i$ and j) Derivation of functional parameters and graphical representation (as is conventional with perfusion CT).

Alternatively, the following steps can also be implemented in accordance with the invention:

a) Start a contrast agent injection
b) Await a delay time (delay) $\Delta T$,
c) Record the rotational exposures during rotational runs with an alternating rotational direction from a starting position (e.g. 0°),
d) Optional pause of any length,
e) Start a second contrast agent injection,
f) Await a delay time (delay) $\Delta T$,
g) Record the rotational exposures during rotational runs with an alternating rotational direction from a final position (e.g. 180°+fan angle),
h) Interpolation of rotational exposures at fixed times $t_i$ from the two perfusion measurements,
i) Reconstruction of three-dimensional data records at times $t_i$ and
j) Derivation of functional parameters and graphical representation (as is conventional with perfusion CT).

BRIEF DESCRIPTION OF THE DRAWINGS

The invention is described in more detail below with reference to the exemplary embodiments shown in the drawings, in which.

DETAILED DESCRIPTION OF THE INVENTION

Figure 1:
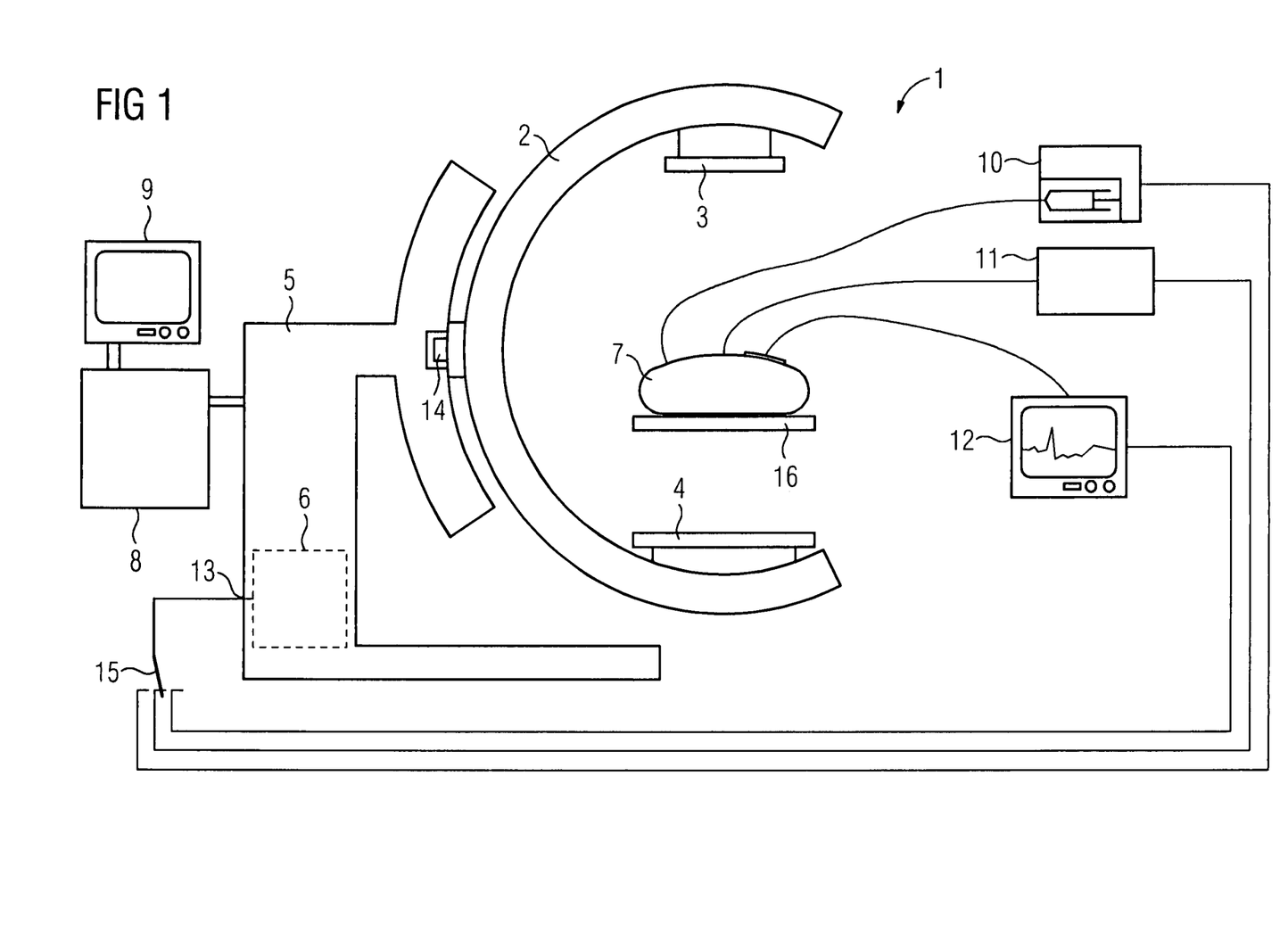
FIG. 1 shows a schematic view of an x-ray C-arm system for implementing the method according to the invention.

The invention is described as exemplified by an x-ray C-arm system 1 with reference to FIG. 1, in which an x-ray tube 3 and an x-ray detector 4 are affixed opposite one another on a C-arm 2 as an image recording unit. The C-arm 2 is attached to a supporting stand 5 and can be moved by means of a control and regulating module 6. An examination object 7, for instance a patient, is positioned on a patient support couch 16 for examination purposes in the pivotal point of the C-arm 2, which can be freely rotated about the examination object 7.

During a movement of the C-arm 2, a rotational run, the examination object 7 can be x-rayed from different projection angles. An image data computer 8 can reconstruct a three-dimensional image data record from a plurality of such projection images, a so-called rotational exposure and display it on a monitor 9.

A contrast agent injector 10, a stimulator 11 and an ECG device 12 or a comparable measuring instrument for recording and evaluating runs of an object of interest with a structure within the examination object 7 can be connected to the examination object 7. The respective device is connected to the signal input 13 of the control and regulating model 6 of the x-ray C-arm system 1 by way of a suitable signal output by means of a switch 15 for instance. An angle sensor 14 for detecting the rotation angle during a rotational run is assigned to the C-arm 2.

Since the number N of necessary rotational runs was determinate particularly as a function of the run speed of the periodic process and the travel speed of the C-arm 2, a differential angle is determined from this information which determines the start angle $\phi_0$ for each rotational run and adjusts the C-arm 2 for the rotational run by means of the control and regulating module 6 with the aid of the angle sensor 14. Depending on which process is to be represented, the contrast agent injector 10, the stimulator 11 or the ECG device 12 or the comparable measuring instrument for recording and evaluating sequences of the object of interest is connected to the structure within the examination object 7.

In order to be able to map the propagation processes of the contrast agent in tissue and/or in organs, the so-called perfusion, the concentration of the contrast agent in the tissue is measured as a function of the time. As these propagation processes take place very quickly in the majority of tissues (5 to 30 seconds), as close a temporal scanning of the contrast agent process as possible poses a significant challenge.

To detect the contrast agent concentration in a quantitative fashion, it is necessary to generate an accurate three-dimensional reconstruction of the contrast agent distribution. To this end, it is necessary to record projections through the object from an angular range of approximately 200° (180°+fan angle), the so-called rotational runs and to reconstruct a three-dimensional volume image herefrom.

Two problems essentially arise here:
The projection images, which are used for a reconstruction, are not recorded at the same time (data inconsistency).
The recording of a three-dimensional data record using a C-arm system requires approximately 4 to 10 seconds. A temporal scanning value can thus only be measured every 4 to 10 seconds.

Figure 2:
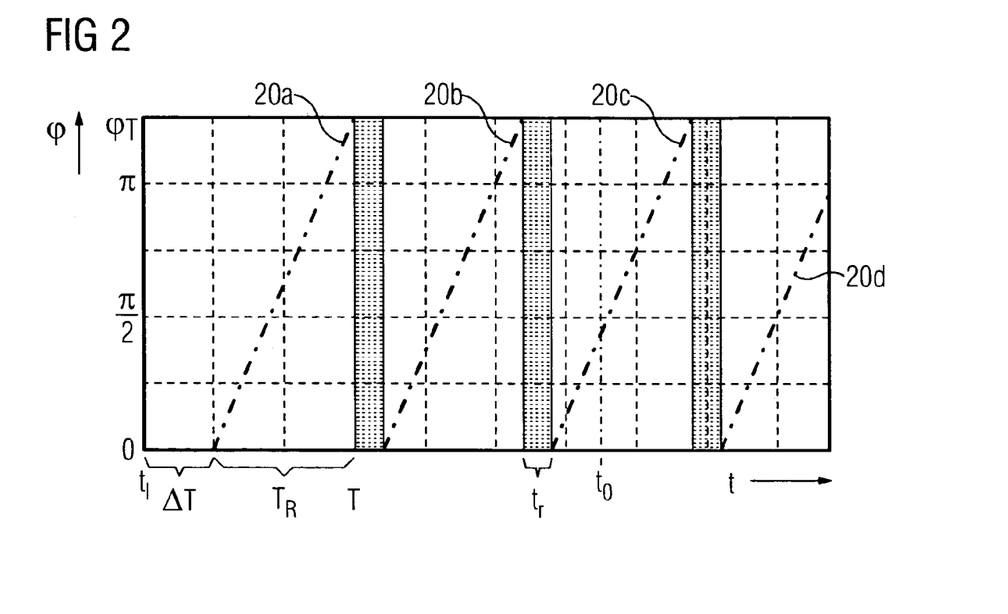
FIG. 2 shows a graphical representation of a perfusion measurement consisting of four rotational runs in the same direction in respect of the recording angle.
Figure 3:
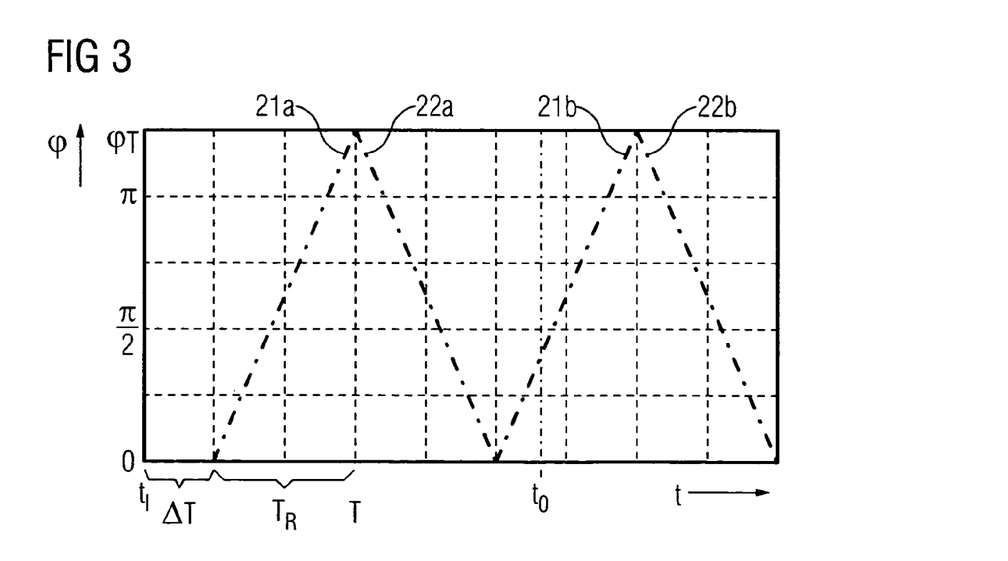
FIG. 3 shows a graphical representation of a perfusion measurement consisting of four rotational runs in the opposite direction in respect of the recording angle.

If a number of rotational exposures are implemented consecutively, as is required for the perfusion measurement, the individual projections in respect of recording time and recording angle ($\phi$) can be graphically represented according to FIGS. 2 and 3.

FIG. 2 shows a schematic representation of the dependency of the recording angle ($\phi$) of the C-arm 2 plotted on the y-axis over the time t plotted on the x-axis. In a first examination sequence, the rotational exposure can always be implemented in the same direction. Each rotational run is thus represented by a slanted ascending dot and dash line 20a, 20b, 20c and 20d. After injection by means of the contrast agent injector 10 at time $t_1$, the first rotational run is started after an adjustable delay time (delay) $\Delta T$, with projection images being created at different angles. This is shown by means of the line 20a, which starts at $t=\Delta T$ as well as at a specific recording angle, the start angle $\phi_0$, and ends at $t=T$ (duration of a rotational run $T_R$ of 4 to 5 seconds for instance) and a higher recording angle of $1.25\pi$ for instance, the end angle $\phi_T$. Temporal gaps result here for the return motion, the return motion time $t_r$.

In a second examination sequence, the individual projection images are recorded in opposite rotational runs, so that no empty return motions are needed, as is shown in FIG. 3, in which the angulation is plotted over the time t. Each rotational run is alternately illustrated by a slanted ascending and/or slanted descending dot and dash line 21a, 21b, 22a and 22b.

To reconstruct a three-dimensional data record, a rotational exposure at a fixed time $t_0$ can now be interpolated from the measured rotational exposures or estimated with a suitable method, like for instance nearest-neighbor-, linear-, spline-interpolation or curve fitting with suitable functions. It should be noted here that the measured times of a projection are not equidistant in the case of an alternating rotational direction.

Any number of times can in principle interpolate in this way; the scanning of the perfusion process is however not changed.

To be able to represent temporally quick processes in a sufficiently effective fashion, it is necessary to improve the actual temporal scanning of the process. The technical limitations of the x-ray C-arm system does not render this readily possible with an individual perfusion measurement.

Figure 4:
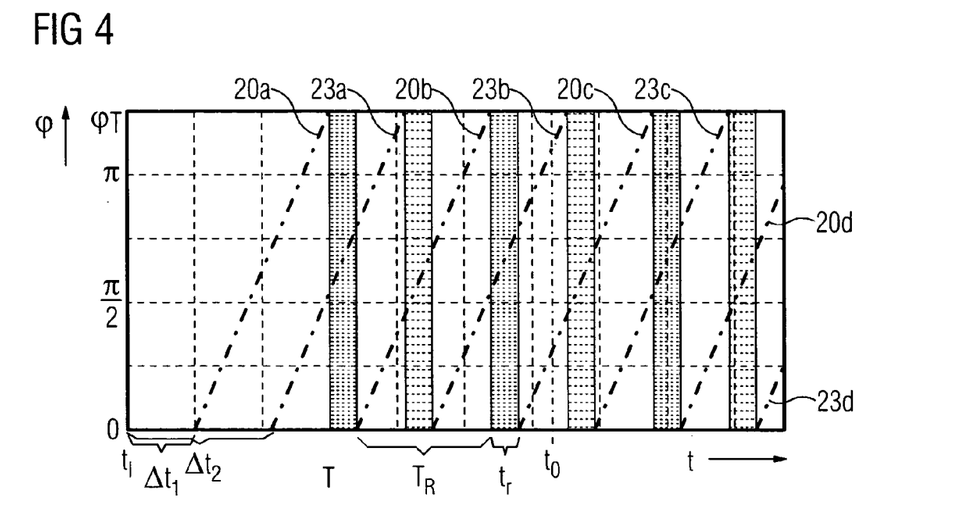
FIG. 4 shows a graphical representation of two inventive perfusion measurements, each with four rotational runs in the same direction in respect of the recording angle.
Figure 5:
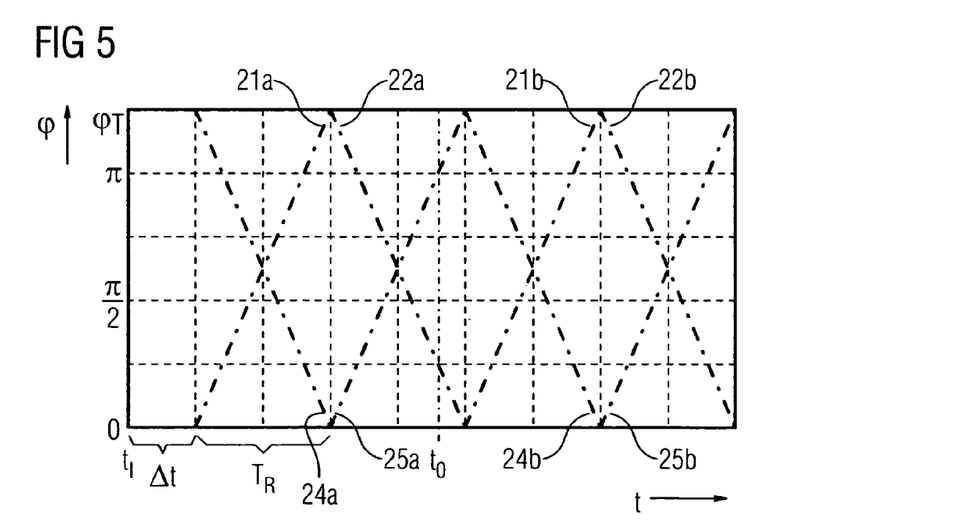
FIG. 5 shows a graphical representation of two inventive perfusion measurements, each with four rotational runs in the opposite direction in respect of the recording angle.

If the assumption is made that the tissue is again completely in the initial state following the perfusion measurement, additional data can be recorded in a second perfusion measurement after a second injection of contrast agent. FIGS. 4 and 5 indicate with a dashed line how additional data can be obtained expediently using a second perfusion measurement.

Here the dot and dash lines 20a, 20b, 20c and 20d in FIG. 4 show the rotational run for the first rotational exposures using a first contrast agent fill according to FIG. 2.

The delay time (delay) ΔT1 from the first contrast agent injection to the first rotational run is determined from the time of the first appearance of the contrast agent in the region of interest (ROI). In the exemplary embodiment according to FIG. 4, the rotational direction of all rotational exposures is identical. The delay ΔT2 between the contrast agent injection and the recording sequence with the second perfusion measurement is to be increased by a half a duration of a complete rotational run (rotation duration $T_R$ including return motion $t_r$) compared with the first perfusion measurement so that the delay ΔT2 with the second contrast agent injection results from:

$$\Delta T2 = \Delta T1 + \frac{1}{2} * (t_R + t_r).$$

In general, $$\Delta Tn = \Delta T1 + \frac{1}{N} * (t_R + t_r)$$

can apply to N rotational runs for the nth rotational run.

The slanted inclining lines 23a, 23b, 23c and 23d show the run of the second rotational exposure following a second contrast agent fill.

In FIG. 5, the instance of the opposite rotations is shown as in FIG. 3. The slanted descending dashed lines 24a and 24b as well as the slanted ascending dashed lines 25a and 25b show the run of the second perfusion measurement following a second contrast agent fill. With these opposite rotations, the perfusion measurements are to begin with the same delay ΔT, however with an opposite initial position.

The recording of two perfusion measurements with a suitable temporal position in respect of each other allows the temporal scanning rate to be doubled. This also allows for such perfusion processes, for which a simple perfusion measurement is too slow as a result of technical limitations of the C-arm 2.

Figure 6:
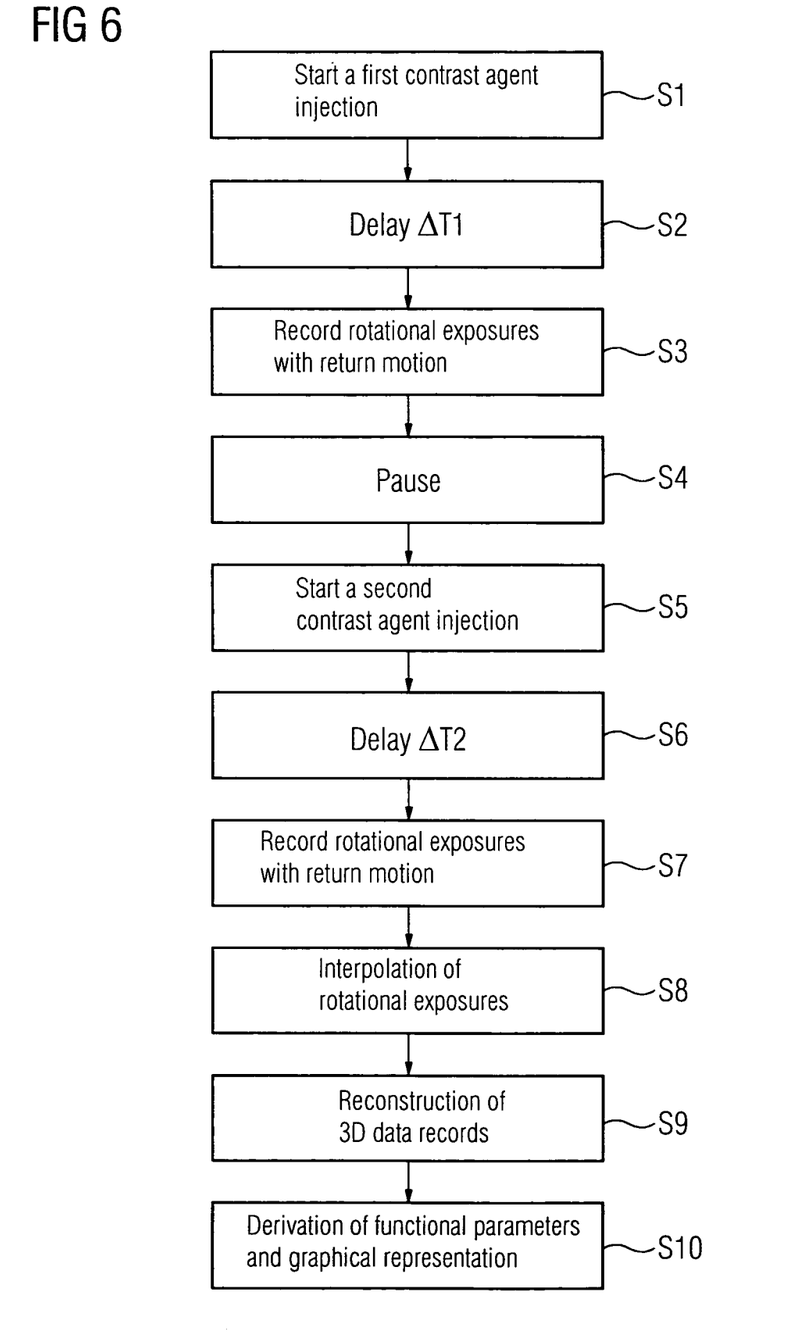
FIG. 6 shows the inventive method sequence to create rotational exposures with the same rotational direction and return motion and FIG. 7 shows the inventive method sequence to create rotational exposures with an alternating rotational direction without return motion.
Figure 7:
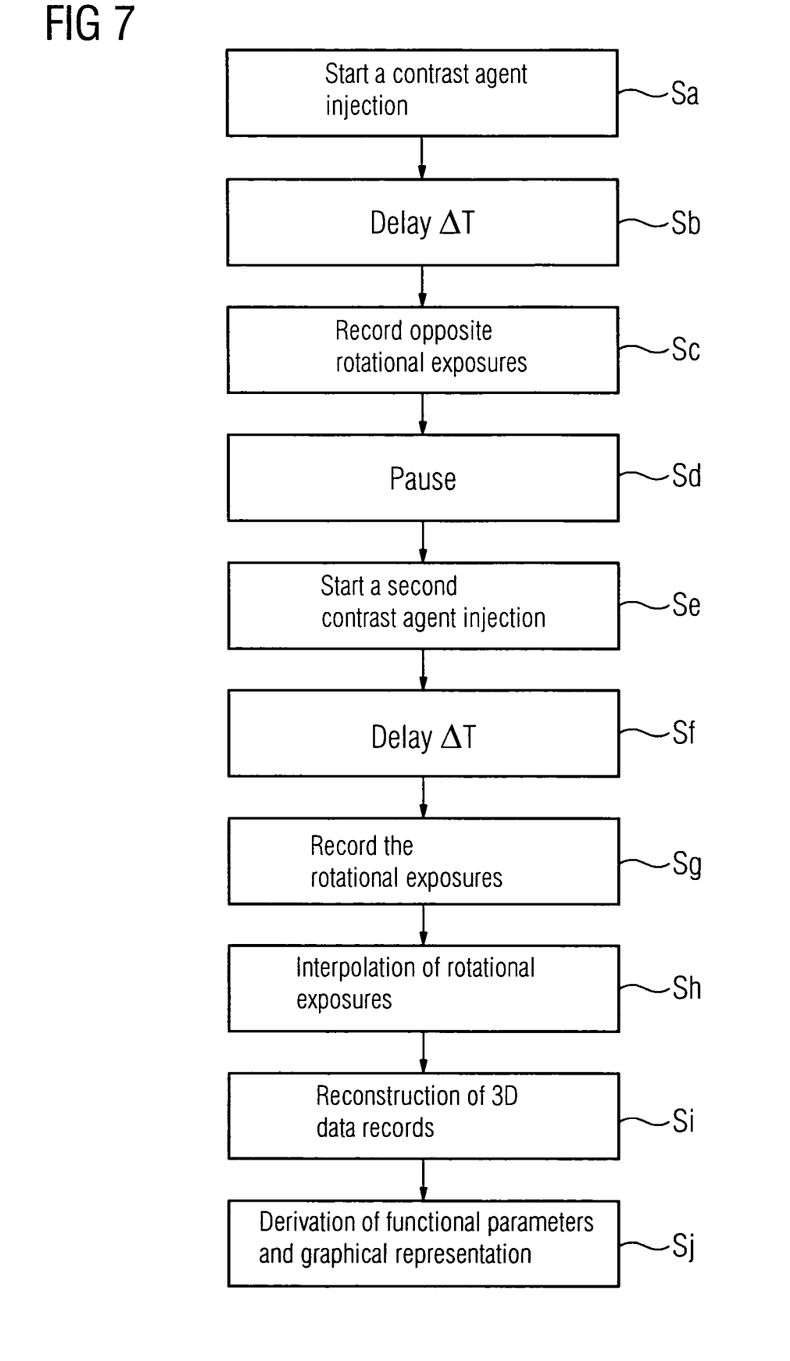

The method sequences according to the invention are described in summary below using the following steps with reference to the FIGS. 6 and 7:

Embodiment 1 (According to FIG. 4)

S1 Start a first contrast agent injection,
S2 Await a delay time (delay) ΔT1,
S3 Record several rotational exposures with the same rotational direction and return motion between the exposures,
S4 Optional pause of any length
S5 Start a second contrast agent injection,
S6 Await a delay time (delay) ΔT2=ΔT1+½*(rotation time+return motion time),
S7 Record several rotational exposures with the same rotational direction and return motion between the recordings,
S8 Interpolation of rotational exposures at fixed time $t_i$ from the two perfusion measurements,
S9 Reconstruction of three-dimensional data records at times $t_i$ and
S10 Derivation of functional parameters and graphical representation (as is conventional with perfusion CT).

Embodiment 2 (According to FIG. 5)

Sa) Start a contrast agent injection,
Sb) Await a delay time (delay) ΔT,
Sc) Record the rotational exposures with an alternating rotational direction from the initial position (e.g. 0°),
Sd) Optional pause of any length,
Se) Start a second contrast agent injection,
Sf) Await a delay time (delay) ΔT,
Sg) Record the rotational exposures with an alternating rotational direction from the final position (e.g. 180°+fan angle),
Sh) Interpolation of rotational exposures at fixed times $t_i$ from the two perfusion measurements,
Si) Reconstruction of three-dimensional data records at the times $t_i$ and
Sj) Derivation of functional parameters and graphical representation (as is conventional with perfusion CT).

In accordance with the invention, the delay ΔT can also be selected to be negative, i.e. that the second run begins temporally prior to the first run by comparison with the injection times. It may even be started before the second injection. An exposure without contrast agent can as a result be created as a mask image.

The invention claimed is:

1. A method for reconstructing a three-dimensional imaging data of a moving structure by a tomographical method, comprising:
    recording a first perfusion measurement with a first contrast agent injection using a first sequence of rotational runs by an imaging recording unit; and
    recording a further perfusion measurement with a further contrast agent injection using a further sequence of rotational runs by the imaging recording unit;
    wherein the further perfusion measurement is started after completion of the first perfusion measurement, and a start time of the further sequence of rotational runs, relative to a time of the further injection, is deviated from a start time of the first sequence of rotational runs relative to a time of the first injection; and
    wherein the first and further sequences of rotational runs are uniformly spaced along a relative time line wherein the respective first and further injection times are overlaid on said relative time line.

2. The method as claimed in claim 1, wherein a plurality of N further perfusion measurements are recorded with the further contrast agent injection and each of the further perfusion measurements comprises recording of an nth sequence of further rotational runs by the imaging recording unit.

3. The method as claimed in claim 2, wherein the sequence of further rotational runs of Nth further perfusion measurement are recorded with an identical rotational direction of the image recording unit.

4. The method as claimed in claim 3, wherein a delay time between the further contrast agent injection and recording of the nth sequence of the further rotational runs is shifted by n/N times the duration of a complete rotational run and a return motion thereof compared with the first perfusion measurement.

5. The method as claimed in claim 3, wherein the further perfusion measurements are recorded with an identical rotational direction of the image recording unit.

6. The method as claimed in claim 5, wherein a delay time between the further contrast agent injection and recording of a subsequent further perfusion measurement is shifted by half a duration of the subsequent further perfusion measurement compared with a preceding perfusion measurement.

7. The method as claimed in claim 6, wherein the duration comprises a rotation duration including return motion.

8. The method as claimed in claim 1, wherein a delay time between the further contrast agent injection and recording of the further perfusion measurement is greater than a delay time between the first contrast agent injection and recording of the first perfusion measurement.

9. The method as claimed in claim 1, wherein a delay time between the further contrast agent injection and recording of the further perfusion measurement is less than a delay time between the first contrast agent injection and recording of the first perfusion measurement.

10. The method as claimed in claim 1, wherein the further perfusion measurement is started temporally prior to the further contrast agent injection.

11. The method as claimed in claim 2, wherein the further perfusion measurements are recorded with opposite rotational directions of the image recording unit.

12. The method as claimed in claim 11, wherein the further perfusion measurements are recorded with same start time of the further contrast agent injection and opposite start angles.

13. The method as claimed in claim 1, further comprising:
starting the first contrast agent injection,
awaiting a delay time ΔT1,
recording rotational exposures during rotational runs of the first perfusion measurement with an identical rotational direction and return motion between the rotational runs,
starting the further contrast agent injection,
awaiting a further delay time ΔT2=ΔT1+1/2*(rotation time+return motion time),
recording further rotational exposures during further rotational runs of the further perfusion measurement with an identical rotational direction and return motion between the further rotational runs,
interpolating the rotational exposures and the further rotational exposures at fixed times from the first and the second perfusion measurements,
reconstructing the three-dimensional data at the fixed times based on the interpolation, and
deriving functional parameters and graphical representation from the three-dimensional data.

14. The method as claimed in claim 1, further comprising:
starting the first contrast agent injection,
awaiting a delay time ΔT,
recording rotational exposures during rotational runs of the first perfusion measurement with an alternating rotational direction from an initial position,
starting the second contrast agent injection,
awaiting the delay time ΔT,
recording further rotational exposures during further rotational runs of the further perfusion measurement with an alternating rotational direction from a final position,
interpolating the rotational exposures and the further rotational exposures at fixed times from the first and the further perfusion measurements,
reconstructing the three-dimensional data at the fixed times based on the interpolation, and
deriving functional parameters and a graphical representation from the three-dimensional data.

15. The method as claimed in claim 1, wherein the further contrast agent injection is paused after the first contrast agent injection.

16. A method for reconstructing a three-dimensional imaging data of a moving structure by a tomographical method, comprising the following sequence of steps:
performing a first contrast agent injection into a patient at a first injection time;
waiting a first delay period ΔT1 relative to the first injection time;
recording medical images of the patient throughout a plurality of first rotational runs of a scan arm of an imaging recording unit, each rotational run spanning from a starting angle to an ending angle of the scan arm;
performing a second contrast agent injection into the patient at a second injection time;
waiting a second delay period ΔT2 relative to the second injection time; and
recording further medical images of the patient throughout a plurality of second rotational runs of the scan arm, each rotational run spanning from the starting angle to the ending angle of the scan atm;
wherein the second delay period ΔT2 is calculated according to the formula:

$$\Delta T2 = \Delta T1 + \frac{1}{2} * (t_R + t_r)$$

wherein $t_R$ represents a time period required for one rotational run of the scan arm from the starting angle to the ending angle thereof, and $t_r$ represents a time period required for a return of the scan arm from the ending angle to the starting angle thereof; and
wherein, on a graph correlating a relative time on an x-axis versus an angle of the scan arm on a y-axis, the plurality of first and second rotational runs are characterized by parallel lines uniformly spaced from each other on the graph, where "relative time" means a time relative to the respective first and second injection times overlaid on the x-axis of the graph.

17. A method for reconstructing a three-dimensional imaging data of a moving structure by a tomographical method, comprising the following sequence of steps:
performing a first contrast agent injection into a patient at a first injection time;
waiting a first delay period ΔT1 relative to the first injection time;
recording medical images of the patient throughout a plurality of first rotational runs of a scan arm of an imaging recording unit, each rotational run spanning from a starting angle to an ending angle of the scan arm;

performing an Nth contrast agent injection into the patient at an Nth injection time, wherein "N" represents an integer of 2 or greater;

waiting an Nth delay period ΔTN relative to the Nth injection time; and recording further medical images of the patient throughout a plurality of Nth rotational runs of the scan arm, each rotational run spanning from the starting angle to the ending angle of the scan arm;

wherein the Nth delay period is calculated according to the formula:

$$\Delta Tn = \Delta T1 + \frac{1}{N} * (t_R + t_r)$$

wherein $t_R$ represents a time period required for one rotational run of the scan arm from the starting angle to the ending angle thereof, and $t_r$ represents a time period required for a return of the scan arm from the ending angle to the starting angle thereof for each of the plurality of first and an Nth of rotational runs.

* * * * *